(12) United States Patent
Chilton

(10) Patent No.: US 6,973,930 B2
(45) Date of Patent: Dec. 13, 2005

(54) PHOTOTHERAPY EYESHIELD FOR BABIES

(75) Inventor: Howard William Chilton, Sydney (AU)

(73) Assignee: Nascor Pty Ltd., New South Wales (AU)

( * ) Notice: Subject to any disclaimer, the term of this patent is extended or adjusted under 35 U.S.C. 154(b) by 63 days.

(21) Appl. No.: 10/257,497

(22) PCT Filed: Apr. 12, 2001

(86) PCT No.: PCT/AU01/00426

§ 371 (c)(1),
(2), (4) Date: Oct. 10, 2002

(87) PCT Pub. No.: WO01/78634

PCT Pub. Date: Oct. 25, 2001

(65) Prior Publication Data

US 2003/0106128 A1    Jun. 12, 2003

(51) Int. Cl.[7] .............................................. A61F 9/00
(52) U.S. Cl. .................... 128/858; 2/12; 2/15
(58) Field of Search ................ 128/857, 858, 128/849; 602/17; 2/6.7, 12, 15

(56) References Cited

U.S. PATENT DOCUMENTS

| | | | | |
|---|---|---|---|---|
| 3,541,608 A | * | 11/1970 | Otwell | 2/15 |
| 3,931,646 A | * | 1/1976 | Loughner | 2/452 |
| 4,331,136 A | * | 5/1982 | Russell et al. | 128/858 |
| 4,411,263 A | * | 10/1983 | Cook | 128/858 |
| 4,502,476 A | * | 3/1985 | Welt | 128/858 |
| 4,502,576 A | | 3/1985 | Reardon | 128/132 R |
| 4,549,793 A | * | 10/1985 | Yoon | 351/156 |
| D285,624 S | * | 9/1986 | Rosenbaum | D16/301 |
| 4,644,588 A | * | 2/1987 | Zawacki | 2/10 |
| 4,670,911 A | * | 6/1987 | Dunford | 2/209 |
| 4,709,695 A | * | 12/1987 | Kohn et al. | 128/858 |
| 4,790,031 A | * | 12/1988 | Duerer | 2/439 |
| 4,912,777 A | * | 4/1990 | Gasbarro | 2/2.15 |
| 4,989,274 A | * | 2/1991 | Patelski, III | 2/436 |
| 5,093,940 A | * | 3/1992 | Nishiyama | 2/441 |
| D325,590 S | * | 4/1992 | Galy | D16/311 |
| 5,105,475 A | * | 4/1992 | Lynd et al. | 2/10 |

(Continued)

FOREIGN PATENT DOCUMENTS

GB    2 234 176    1/1991

OTHER PUBLICATIONS

"Wee Specs®"; Internet Advertisement; Children's Medical Ventures; downloaded Nov. 4, 2004; http://www.childmed.com/product_info/product.cfm?p=19723D0A-6AC3-457C-B8EAA8.

(Continued)

*Primary Examiner*—Henry Bennett
*Assistant Examiner*—Camtu Nguyen
(74) *Attorney, Agent, or Firm*—Gordon & Jacobson, P.C.

(57) ABSTRACT

An eyeshield (10) for protecting babies' eyesight during phototherapy treatment for neonatal jaundice includes a strap (11) of soft material sized and shaped to pass around and secured to the head of the baby. An eye pad (18) is attached or formed integrally with the strap (11). A tab (13) extending from the strap (11) adjacent to the eye pad (18) can be grasped to aid in positioning the eyeshield (10) such that the eye pad (18) lies over the baby's eyes.

51 Claims, 3 Drawing Sheets

U.S. PATENT DOCUMENTS

| | | | | |
|---|---|---|---|---|
| 5,129,106 | A | * | 7/1992 | Liou ............................... 2/411 |
| 5,184,354 | A | * | 2/1993 | Alfaro et al. ................... 2/425 |
| 5,226,992 | A | * | 7/1993 | Morman .................... 156/62.4 |
| 5,384,605 | A | * | 1/1995 | Escobosa .................... 351/123 |
| 5,613,502 | A | * | 3/1997 | Lee ............................. 128/857 |
| 5,636,388 | A | * | 6/1997 | Hodges ......................... 2/443 |
| D385,661 | S | * | 10/1997 | Moorhouse ................ D29/104 |
| D389,636 | S | * | 1/1998 | Davis, Sr. .................... D2/894 |
| 5,713,078 | A | * | 2/1998 | DeAngelis ..................... 2/209 |
| 5,768,715 | A | * | 6/1998 | Gregg, III et al. ............... 2/411 |
| 5,870,849 | A | * | 2/1999 | Colson, Jr. ................... 43/25.2 |
| 6,223,748 | B1 | * | 5/2001 | Chaves et al. .............. 128/857 |
| 6,449,777 | B1 | * | 9/2002 | Montague ...................... 2/452 |
| 6,751,811 | B1 | * | 6/2004 | Hill ............................... 2/453 |

OTHER PUBLICATIONS

"Baby Shades™", Internet Advertisement; Kendall LTP; downloaded Oct. 26, 2004; http://www.kendall-ltp.com/neoshade.htm.

"Neoshades", Internet Advertisement; Neotech Products, Inc.; downloaded Oct. 28, 2004;http://www.neotechproducts.com/store/detail.php?sku=NT—10 &session.

"Posey Phototherapy Eye Protectors"; Internet Ad; NICU/Pediatric; downloaded Oct. 28, 2004; http://www.posey.com/products/4644.html.

* cited by examiner

PHOTOTHERAPY EYESHIELD FOR BABIES

FIELD OF THE INVENTION

The present invention relates to eyeshields. More particularly, though not exclusively, the invention relates to a shield for protecting babies' eyesight during phototherapy treatment for neonatal jaundice.

Jaundice is the yellow discolouration of skin and tissues from the deposition in them of the fat-soluble pigment bilirubin excreted by the liver. Jaundice is not uncommon in newborn infants (pre-term or full-term) when the liver is not physiologically mature, and results from the bile produced by the liver passing into the bloodstream instead of into the intestines.

Treatment of neonatal jaundice consists of phototherapy, the exposing of the afflicted infant to visible blue light of wavelength 425–475 nm. Light of that wavelength converts the fat-soluble bilirubin into intermediary, photobilirubin isomers which are water soluble. The water-solubility of the photobilirubins enables that pigment to be excreted easily, unlike the fat-soluble bilirubin which must pass through the liver and be converted (conjugated) into the water-soluble bilirubin diglucuronide before it can be excreted.

During phototherapy treatment of jaundiced infants, it normally is desirable to place shields or shades over the eyes of the infant to protect the eyes from the blue light.

Prior art eyeshades include self-adhesive shades which are affixed to the infant's temples and are kept in place with the use of a headband attached to the eyeshade by means of fabric fasteners such as Velcro™.

Disadvantages of the known phototherapy eyeshades are that they tend to slip down away from the infant's eyes due to failure of the adhesive and the slipping of the headband, due to the infant's natural movement during sleep and waking periods.

It thus would be advantageous to have a phototherapy eyeshield which remains securely fastened over the infant's eyes, and which does not require adhesive to be placed onto the infant's skin. A further advantage is that the eyeshield should be made of an inert, absorptive fabric to minimise the build up of "sticky eye" discharge which is common in the first few days following the baby's birth.

OBJECT OF THE INVENTION

It is the object of the present invention to overcome or substantially ameliorate at least one of the above disadvantages and/or more generally to provide an improved eyeshield.

DISCLOSURE OF THE INVENTION

There is disclosed herein an eyeshield, comprising:
a strap of soft material sized and shaped to pass around and secure to the head of a wearer,
an eye pad or pads attached to or formed integrally with the strap, and
a tab extending from the stray adjacent to the eye pad(s), which tab can be grasped to aid in positioning the eyeshield such that the eye pad(s) lie(s) over the wearer's eyes.

Preferably the tab extends away from the wearer's face is use.

Preferably the eyeshield also includes a band extending from the strap and configured to lie over the forehead of the wearer in use.

Preferably the band includes a second tab which extends away from the wearer's forehead in use, which second tab can be grasped to aid in positioning the eyeshield.

Preferably the eye pad is attached to the strap.

Preferably the strap is stretchable.

Preferably the material from which the strap and band are made is a non-woven fabric.

A fabric suitable for the strap and bind is known as "SBL" manufactured by the Kimberly Clark Corporation.

Preferably the eye pad when compared with the material from which the strap and band are made, is relatively non-stretchable.

Preferably the eye pad(s) is/are replaceable and temporarily secured to the strap.

Preferably fabric fasteners are used to attach the eye pad(s) to the strap.

Preferably the strap has two ends which are temporarily mutually attachable by means of a fabric fastener.

Preferably the eye pad(s) is/are made of a liquid-absorptive material.

Preferably the eye pad has low light transmissibility.

More preferably, the eye pad is opaque.

The eye pad might typically be formed of felt.

Preferably, the eye pad is sized and shaped to include portions that cover the eyes of the wearer, the eye pad being attached to the strap at a position that will be between the wearer's eyes in use of the eyeshield, such that any stretching of the strap does not stretch said portions of the pad.

The eye pad might be formed as a laminate of felt and opaque material. For example, the laminate might be a laminate of felt-Mylar™-felt.

Preferably the eyeshield is formed from pieces of material stitched and/or welded together.

It might be desirable to have ear muffs attached to or formed integrally with the strap. Such ear muffs might be suitable for premature babies in noisy incubators or for babies being transported in helicopters for example.

The wearer might typically be an infant undergoing phototherapy, but might alternatively be an adult or child say as a passenger in an aircraft or using a sun tanning solarium for example.

There is further disclosed herein a method of protecting a wearer's eyes, the method including:
attaching the above-disclosed eyeshield to the wearer's head by passing the strap around the head, and
grasping the tab to position the eyeshield such that the eye pad(s) lie(s) over the wearer's eyes.

There is further disclosed herein an eyeshield comprising:
a strap of soft, stretchable material sized and shaped to pass around and secure to the head of a wearer,
an eye pad sized and shaped to include portions that cover the eyes of the wearer, the eye pad being attached or attachable to the strap at a position that will be between the wearer's eyes in use of the eyeshield, such that stretching of the strap does not stretch said portions of the eye pad.

Preferably the eyeshield further includes a tab extending from the strap at a position that will be between the wearer's eyes in use of the eyeshield.

Preferably the tab extends away from the wearer's face is use.

Preferably the eyeshield also includes a band extending from the strap and configured to pass over the forehead of the wearer in use.

Preferably the band includes a second tab which extends away from the wearer's forehead in use.

Preferably the material from which the strap and band are made is a non-woven fabric.

A fabric suitable for the strap and band is known as "SBL" manufactured by the Kimberly Clark Corporation.

Preferably the eye pad when compared with the material from which the strap and band are made, is relatively non-stretchable.

Preferably the eye pad is replaceable and temporarily secured to the strap.

Preferably a fabric fastener is used to attach the pad to the strap.

Preferably the strap has two ends which are temporarily mutually attachable by means of a fabric fastener.

Preferably the eye pad is made of a liquid-absorptive material.

Preferably the eye pad has low light transmissibility.

More preferably, the eye pad is opaque.

The eye pad might typically be formed of felt.

The eye pad might be formed as a laminate of felt and opaque material. For example, the laminate might be a laminate of felt-Mylar™-felt.

Preferably the eyeshield is formed from pieces of material stitched and/or welded together.

It might be desirable to have ear muffs attached to or formed integrally with the strap. Such ear muffs might be suitable for premature babies in noisy incubators or for babies being transported in helicopters for example.

The wearer might typically be an infant undergoing phototherapy, but might alternatively be an adult or child say as a passenger in an aircraft or using a sun tanning solarium for example.

There is further disclosed herein a method of protecting a wearer's eyes, the method including: securing the above disclosed eyeshield to the wearer's head by passing the strap of soft, stretchable material around the head and positioning the eye pad over the eyes.

The wearer might typically be an infant undergoing phototherapy, but might alternatively be an adult or child say as a passenger in an aircraft or using a sun tanning solarium for example.

There is further disclosed herein an eyeshield comprising:
a strap sized and shaped to pass around and secure to the head of a wearer such that a portion of the strap passes across the eyes of the wearer,
a band extending from the strap and sized, shaped and configured to lie across the forehead of the wearer to assist in retaining the strap in place, and
an eye pad or pads attached to or formed integrally with the strap so as to cover the eyes in use.

Preferably the strap includes a tab that can be grasped by a person to assist in positioning the strap.

Preferably the band includes a tab, similar in use and purpose to the tab of the strap.

Preferably the tabs extend away from the wearer's face is use.

Preferably the strap and band are stretchable.

Preferably the material from which the strap and band are made is a non-woven fabric.

A fabric suitable for the strap and band is known as "SBL" manufactured by the Kimberly Clark Corporation.

Preferably the eye pad when compared with the material from which the strap and band are made, is relatively non-stretchable.

Preferably, the eye pad is sized and shaped to include portions that cover the eyes of the wearer, the eye pad being attached to the strap at a position that will be between the wearer's eyes in use of the eyeshield such that any stretching of the strap does not stretch said portions of the pad.

Preferably the pad is replaceable and temporarily secured to the strap.

Preferably a fabric fastener is used to attach the pad to the strap.

Preferably the strap has two ends which are temporarily mutually attachable by means of a fabric fastener.

Preferably the pad is made of a liquid-absorptive material.

Preferably the pad hits low light transmissibility.

More preferably, the eye pad is opaque.

The eye pad might typically be formed of felt.

The eye pad might be formed as a laminate of felt and opaque material. For example, the laminate might be a laminate of felt-Mylar™-felt.

Preferably the eyeshield is formed from pieces of material stitched and/or welded together.

It might be desirable to have ear muffs attached to or formed integrally with the strap. Such ear muffs might be suitable for premature babies in noisy incubators or for babies being transported in helicopters for example.

The wearer might typically be an infant undergoing phototherapy, but might alternatively be an adult or child say as a passenger in an aircraft or using a sun tanning solarium for example.

There is further disclosed herein a method of protecting a wearer's eyes, the method including passing the strap of the above disclosed eyeshield around the wearer's head and positioning the eye pad or pads so as to cover the eyes, and positioning the band so as to lie across the forehead of the wearer to assist in retaining the strap in place.

The wearer might typically be an infant undergoing phototherapy, but might alternatively be an adult or child say as a passenger in an aircraft or using a sun tanning solarium for example.

BRIEF DESCRIPTION OF THE DRAWINGS

A preferred form of the present invention will now be described by way of example with reference to the accompanying drawings wherein.

DESCRIPTION OF THE PREFERRED EMBODIMENT

Figure 1:
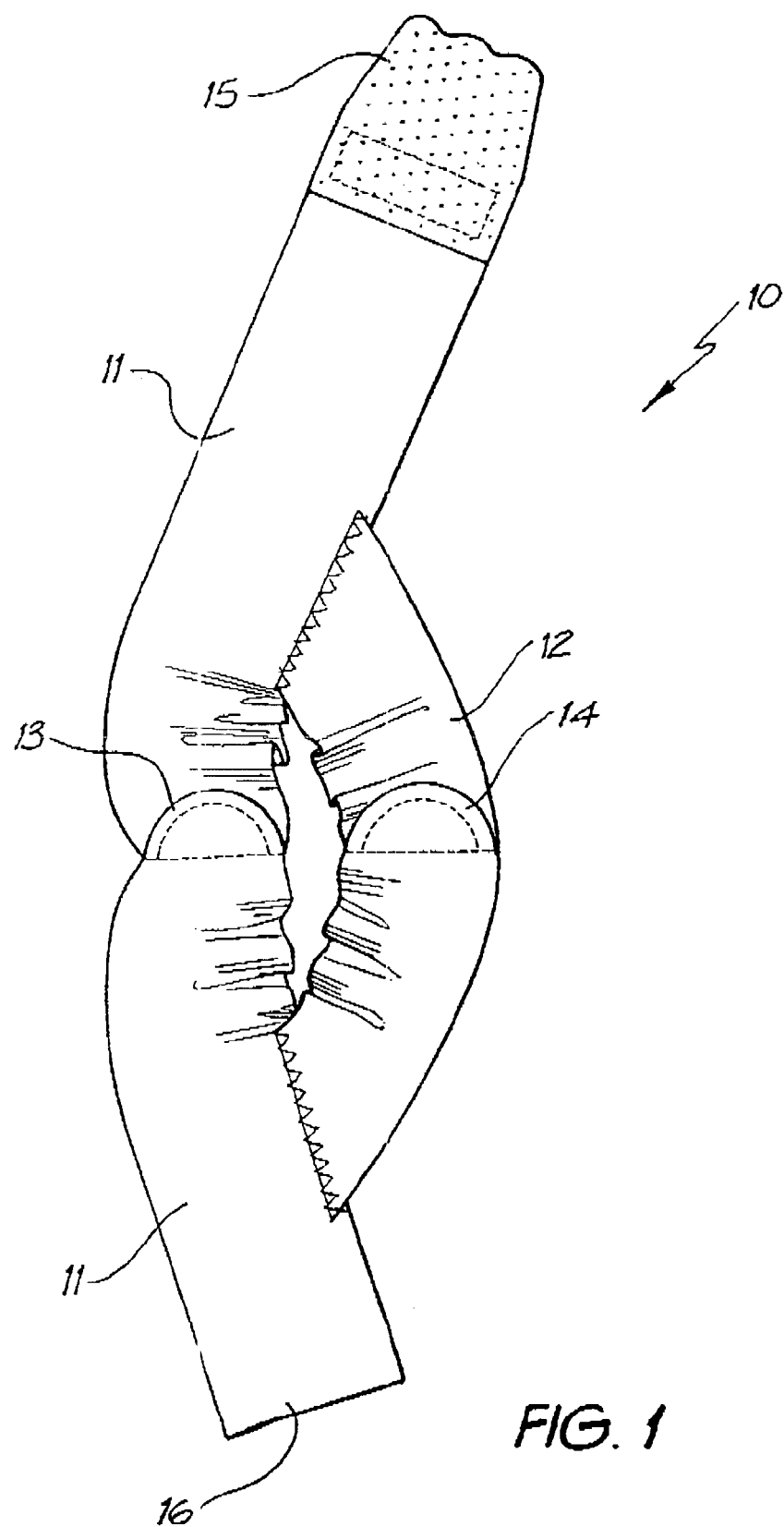
FIG. 1 is a schematic plan view of an eyeshield for infants.

In the accompanying drawings there is schematic depicted an eyeshield 10. The eyeshield includes a strap 11 and a band at 12 stitched to the strap 11. Both the strap and the band are typically made of a soft material that stretches in the band length direction but does not substantially stretch in the cross band direction. Non-woven fabrics are particular suitable for this purpose. An example of such a fabric is known as "SBL" manufactured by the Kimberly Clark Corporation.

The strap 11 has a tab 13 extending from a substantially centralised portion thereof. The tab 13 is sized to be grasped between the thumb and finger of an adult. It should be noted that the strap 11 is of a sufficient length to wrap circumferential around a baby's head. One cad of the strap 11 is provided with a fabric fastener 15, typically a Velcro™ fastener. The fabric fastener is designed to temporary secure to the end 16 of strap 11 in use of the eyeshield.

The band 12 also includes a tab 14 sized to be grasped between the thumb and finger of an adult.

Figure 2:
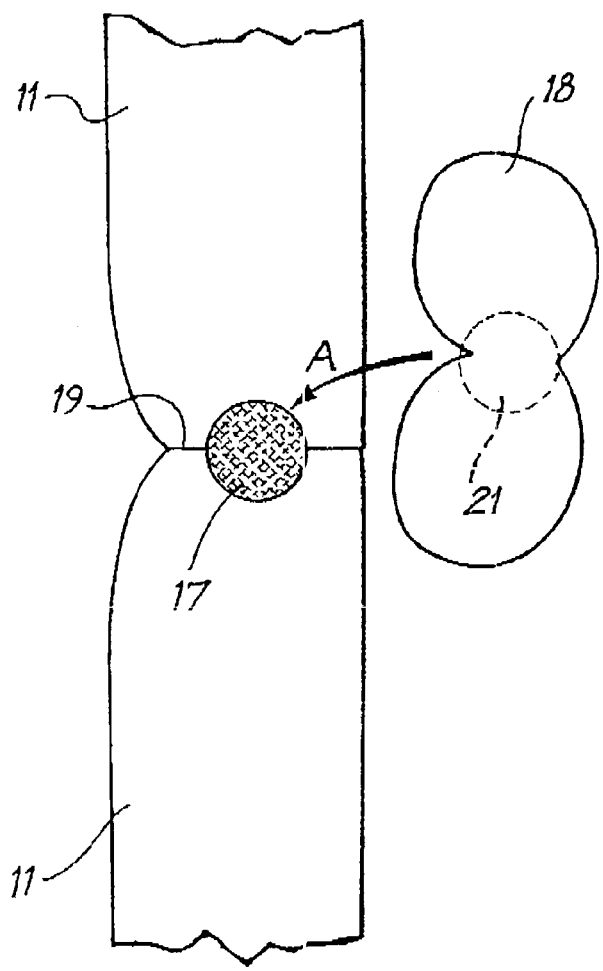
FIG. 2 is a schematic inverted plan view of a portion of the eyeshield of FIG. 1 and an eye pad attachable thereto.

As shown in FIG. 2, the strap 11 (shown in an inverted orientation) includes at its central portion a fabric fastening spot 17. This spot might be a Velcro™ fastener. This fastening spot night be glued, welded, stitched otherwise attached to the strap 11.

Figure 3:
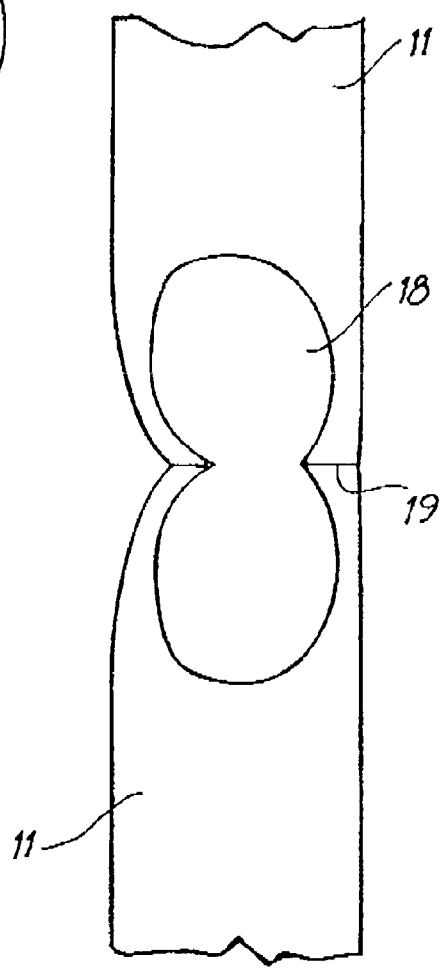
FIG. 3 is a schematic inverted plan view of the portion of the eyeshield shown in FIG. 2, although with the eye pad affixed in place.

In the preferred embodiment, the strap 11 is formed of two lengths joined at a seam 19. The tab 13 might simply be formed as a pair of end portions of the respective strap portion 11 stitched together and extending upwardly from the seam 19. The purpose of the fabric spot 17 is to act as a connector by which an eye pad 18 can be temporarily secured to the strap 11. The eye pad 18 might be formed of felt or a laminate as disclosed above. The portion of the eye pad shown as a dotted circle 21 is intended to be pressed on to the fastening spot 17 in the direction indicated by arrow A. The attached configuration of the eye pad with respect to the strap 11 is depicted in FIG. 3.

Figure 4:
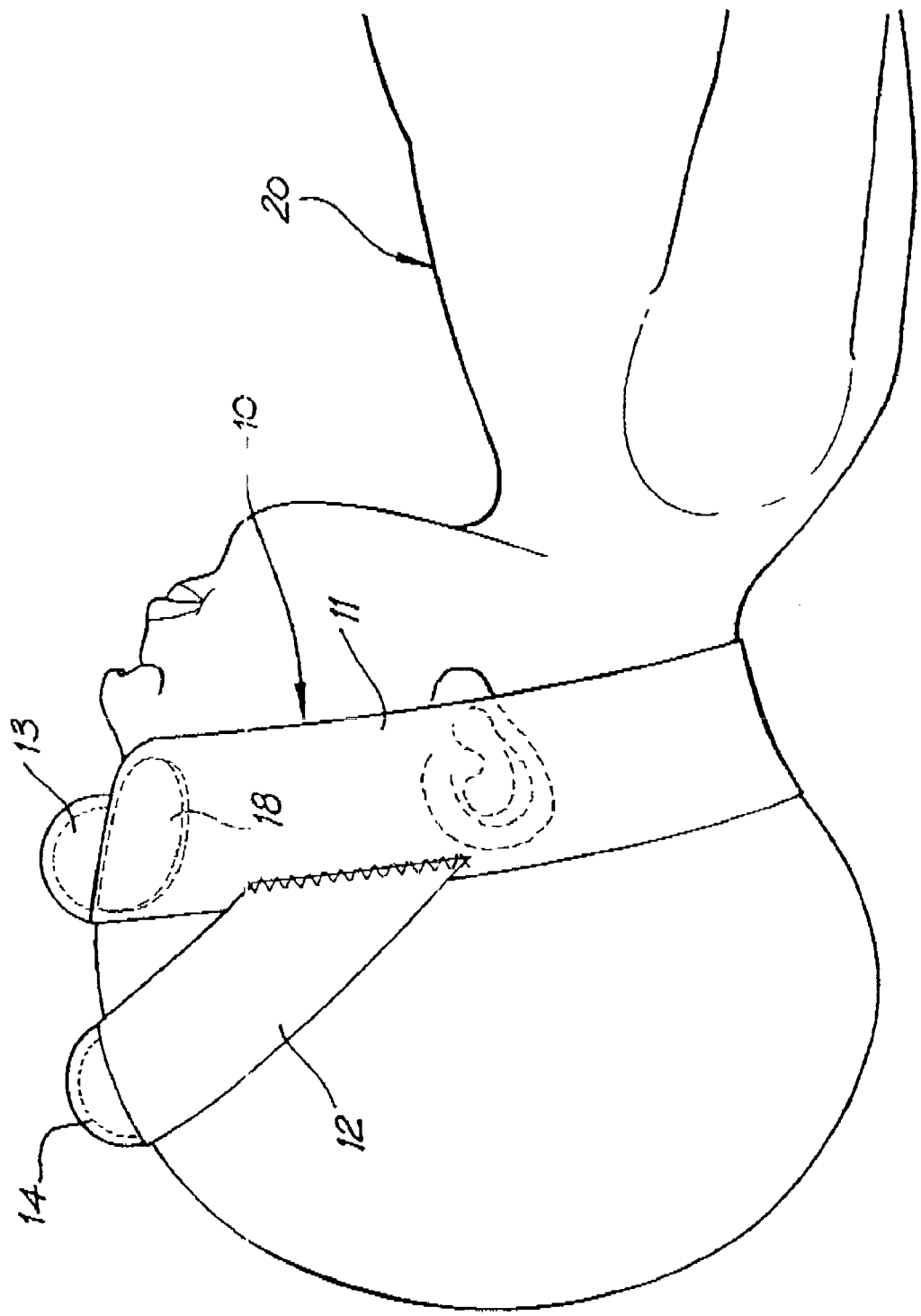
FIG. 4 is a schematic side elevational view of a baby's head with the eyeshield of FIGS. 1–3 position thereon.

In FIG. 4 there is schematically depicted in side elevation the head of a baby 20 onto which there is attached the eyeshield 10. As can be seen, the strap 11 extends about the infant's head below this occipital bulge with the eye pad 18 overlining the infant's eyes.

The band 12 extending from the strap 11 passes over the forehead of the infant. Both tabs 13 and 14 can be gasped by a person to aid in positioning the eye pad 18 over the infant's eyes and in making the overall eyeshield snugly fit the infant's head for comfort.

The infant now can be provided with the appropriate phototherapy treatment.

If the infant suffers from weeping or sticky eyes, the exudate can be absorbed by the eye pad 18 and the eye pad can be replaced by simply removing it from the fastening spot 17.

In stretching or moving the strap 11, the portions of the eye pad 18 which overlie the infant's eyes are not stretched. This is because it is only the central portion of the eye pad that is affixed to the strap 11 via the fastening spot 17.

It should be appreciated that modifications and alterations obvious to those skilled in the art enough to be considered as beyond the scope of the present invention. For example, the seam 19 and/or fastening spot 17 need not be substantially centralised along the strap 11 as it might be more desirable to provide a fabric fastener 15 which would reside to the side of the infant's head, rather than behind the head where it might press against the surface upon which the head is resting.

Furthermore the strap 11 might be provided with two ear muffs, each of which would be position to overlie the infant's ears for protection of premature infants in incubators or infants being transported in helicopters for example.

What is claimed is:

1. An eyeshield, comprising:
    a strap of soft material sized and shaped to pass around and secure to the head of a wearer,
    a band extending from the strap on opposite sides of the wearer's head and configured to lie over the wearer's forehead in use;
    an eye pad or pads attached to or formed integrally with the strap, and
    a tab extending from the strap adjacent to the eye pad(s), which tab can be grasped to aid in positioning the eyeshield such that the eye pad(s) lie(s) over the wearer's eyes.

2. The eyeshield of claim 1, wherein the tab extends away from the wearer's face is use.

3. The eyeshield of claim 1 being formed from pieces of material stitched and/or welded together.

4. The eyeshield of claim 1 wherein the band includes a second tab which extends away from the wearer's forehead in use, which second tab can be grasped to aid in positioning the eyeshield.

5. The eyeshield of claim 1 wherein the eye pad is attached to the strap.

6. The eyeshield of claim 1 wherein the strap is stretchable.

7. The eyeshield of claim 1 wherein the material from which the strap and band are made is a non-woven fabric.

8. The eyeshield of claim 7 wherein the fabric for the strap and band is a stretch-bonded laminate material.

9. The eyeshield of claim 1 wherein the eye pad, when compared with the material from which the strap and band are made, is relatively non-stretchable.

10. The eyeshield of claim 1 wherein the eye pad(s) is/are replaceable and temporarily secured to the strap.

11. The eyeshield of claim 10 wherein fabric fasteners are used to attach the eye pad(s) to the strap.

12. The eyeshield of claim 1 wherein the strap has two ends which are temporarily mutually attachable by means of a fabric fastener.

13. The eyeshield of claim 1 wherein the eye pad(s) is/are made of a liquid-absorptive material.

14. The eyeshield of claim 1 wherein the eye pad has low light transmissibility.

15. The eyeshield of claim 1 wherein the eye pad is opaque.

16. The eyeshield of claim 1 wherein eye pad is formed of felt.

17. The eyeshield of claim 1 wherein the eye pad is sized and shaped to include portions that cover the eyes of the wearer, the eye pad being attached to the strap at a position tat will be between the wearer's eyes in use of the eyeshield, such that any stretching of the strap does not stretch said portions of the pad.

18. The eyeshield of claim 1 wherein the eye pad is formed as a laminate of felt and opaque material.

19. The eyeshield of claim 18 wherein the laminate is a laminate of felt—a biaxially-oriented polyethylene terephthalate polyester film-felt.

20. An eyeshield comprising:
    a strap of soft, stretchable material sized and shaped to pass around and secure to the head of a wearer,
    a band extending from the strap on opposite sides of the wearer's head and configured to lie over the wearer's forehead in use,
    an eye pad sized and shaped to include portions that cover the eyes of the wearer, the eye pad being attached or attachable to the strap at a position that will be between the wearer's eyes in use of the eyeshield, such that stretching of the strap does not stretch said portions of the eye pad, and wherein the eye pad is opaque in order to prevent light passing therethrough.

21. The eyeshield of claim 20 wherein the eye pad is formed as a laminate of felt and opaque material.

22. The eyeshield of claim 21 wherein the laminate is a laminate of felt—a biaxially-oriented polyethylene terephthalate polyester film-felt.

23. The eyeshield of claim 20 further including a tab extending from the strap at a position that will be between the wearer's eyes in use of the eyeshield.

24. The eyeshield of claim 23 wherein the tab extends away from the wearer's face is use.

25. The eyeshield of claim 20 being formed from pieces of material stitched and/or welded together.

26. The eyeshield of claim 24 wherein the band includes a second tab which extends away from the wearer's forehead in use.

27. The eyeshield of claim 20 wherein the material from which the strap and band are made is a non-woven fabric.

28. The eyeshield of claim 27 wherein the non-woven fabric is a stretch-bonded laminate material.

29. The eyeshield of claim 20 wherein the eye pad when compared with the material from which the strap and band are made, is relatively non-stretchable.

30. The eyeshield of claim 29 wherein the eye pad is replaceable and temporarily secured to the strap.

31. The eyeshield of claim 30 wherein a fabric fastener is used to attach the pad to the strap.

32. The eyeshield of claim 20 wherein the strap has two ends which are temporarily mutually attachable by means of a fabric fastener.

33. The eyeshield of claim 20 wherein the eye pad is made of a liquid-absorptive material.

34. The eyeshield of claim 20 wherein the eye pad is formed of felt.

35. An eyeshield comprising:
a strap sized and shaped to pass around and secure to the head of a wearer such that a portion of the strap passes across the eyes of the wearer,
a band extending from the strap and sized, shaped and configured to lie across the forehead of the wearer to assist in retaining the strap in place, and
an eye pad or pads attached to or formed integrally with the strap so as to cover the eyes in use, wherein the eye pad or pads is opaque in order to prevent light passing therethrough.

36. The eyeshield of claim 35 being formed from pieces of material stitched and/or welded together.

37. The eyeshield of claim 35 wherein the eye pad is formed as a laminate of felt and opaque material.

38. The eyeshield of claim 37 wherein the laminate is a laminate of felt—a biaxially-oriented polyethylene terephthalate polyester film-felt.

39. The eyeshield of claim 35 wherein the eye pad is formed of felt.

40. The eyeshield of claim 35 wherein the pad is made of a liquid-absorptive material.

41. The eyeshield of claim 35 wherein the strap has two ends which are temporarily mutually attachable by means of a fabric fastener.

42. The eyeshield of claim 41 wherein the strap includes a tab that can be grasped by a person to assist in positioning the strap.

43. The eyeshield of claim 41 wherein the band includes a tab, similar in use and purpose to the tab of the strap.

44. The eyeshield of claim 43 wherein the tabs extend away from the wearer's face is use.

45. The eyeshield of claim 41 wherein the strap and band are stretchable.

46. The eyeshield of claim 45 wherein the material from which the strap and band are made is a non-woven fabric.

47. The eyeshield of claim 46 wherein the material is a stretch-bonded laminate material.

48. The eyeshield of claim 45 wherein the eye pad when compared with the material from which the strap and band are made, is relatively non-stretchable.

49. The eyeshield of claim 35 wherein the eye pad is sized and shaped to include portions that cover the eyes of the wearer, the eye pad being attached to the strap at a position that will be between the wearer's eyes in use of the eyeshield, such that any stretching of the strap does not stretch said portions of the pad.

50. The eyeshield of claim 35 wherein the pad is replaceable and temporarily secured to the strap.

51. The eyeshield of claim 35 wherein a fabric fastener is used to attach the pad to the strap.

* * * * *